United States Patent
Höijer et al.

(10) Patent No.: US 7,020,522 B1
(45) Date of Patent: Mar. 28, 2006

(54) DUAL CHAMBER HEART STIMULATOR WITH EVOKED RESPONSE DETECTOR

(75) Inventors: Carl Johan Höijer, Malmö (SE); Martin Obel, Danderyd (SE)

(73) Assignee: St. Jude Medical AB, (SE)

( * ) Notice: Subject to any disclaimer, the term of this patent is extended or adjusted under 35 U.S.C. 154(b) by 467 days.

(21) Appl. No.: 10/070,470

(22) PCT Filed: Sep. 6, 2000

(86) PCT No.: PCT/SE00/01714

§ 371 (c)(1),
(2), (4) Date: Jul. 3, 2002

(87) PCT Pub. No.: WO01/17608

PCT Pub. Date: Mar. 15, 2001

(30) Foreign Application Priority Data

Sep. 9, 1999 (SE) .................................. 9903205

(51) Int. Cl.
*A61N 1/18* (2006.01)
(52) U.S. Cl. ............................. 607/27; 607/9
(58) Field of Classification Search ............ 607/9, 607/27
See application file for complete search history.

(56) References Cited

U.S. PATENT DOCUMENTS

| | | | |
|---|---|---|---|
| 4,702,253 A | 10/1987 | Nappholz et al. | |
| 5,391,192 A | * 2/1995 | Lu et al. | 607/28 |
| 5,507,782 A | 4/1996 | Kieval et al. | |
| 5,534,016 A | 7/1996 | Boute | |
| 5,626,620 A | 5/1997 | Kieval et al. | |
| 5,713,930 A | 2/1998 | van der Veen et al. | |

* cited by examiner

Primary Examiner—George Manuel
Assistant Examiner—Lenwood Faulcon, Jr.
(74) Attorney, Agent, or Firm—Schiff Hardin LLP

(57) ABSTRACT

A heart stimulator has an atrial and ventricular pulse generator for producing atrial and ventricular stimulation pulses, an atrial sensor for sensing atrial signals and an evoked response detector for detecting the occurrence of incipient fusion beats from measured ventricular signals. A determination unit determines an incipient fusion AV-interval from the sensed atrial signals and the detected fusion beats, and a controller controls the pulse generator to deliver stimulation pulses at a controlled AV-interval which is shorter than the incipient fusion AV-interval. The evoked response detector includes an averaging unit which forms an average amplitude value of the measured ventricular signals during a predetermined time window of each cardiac cycle, and a comparator which compares the average value for each cardiac cycle with a predetermined limit criterion, and supplies the result of the comparison to the determination unit for determining a measured ventricular signal resulted from an incipient fusion beat or a completely stimulated capture.

8 Claims, 3 Drawing Sheets

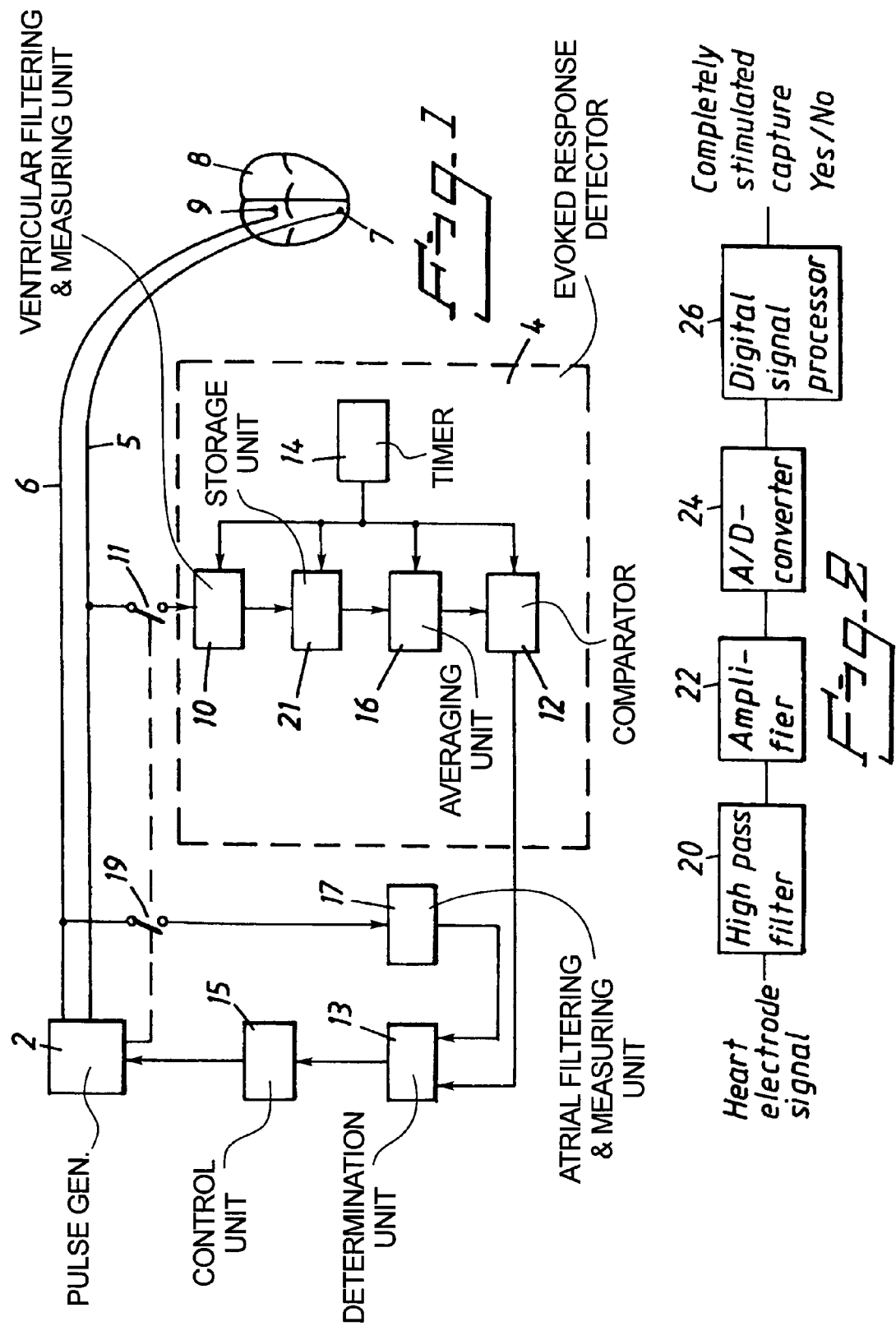

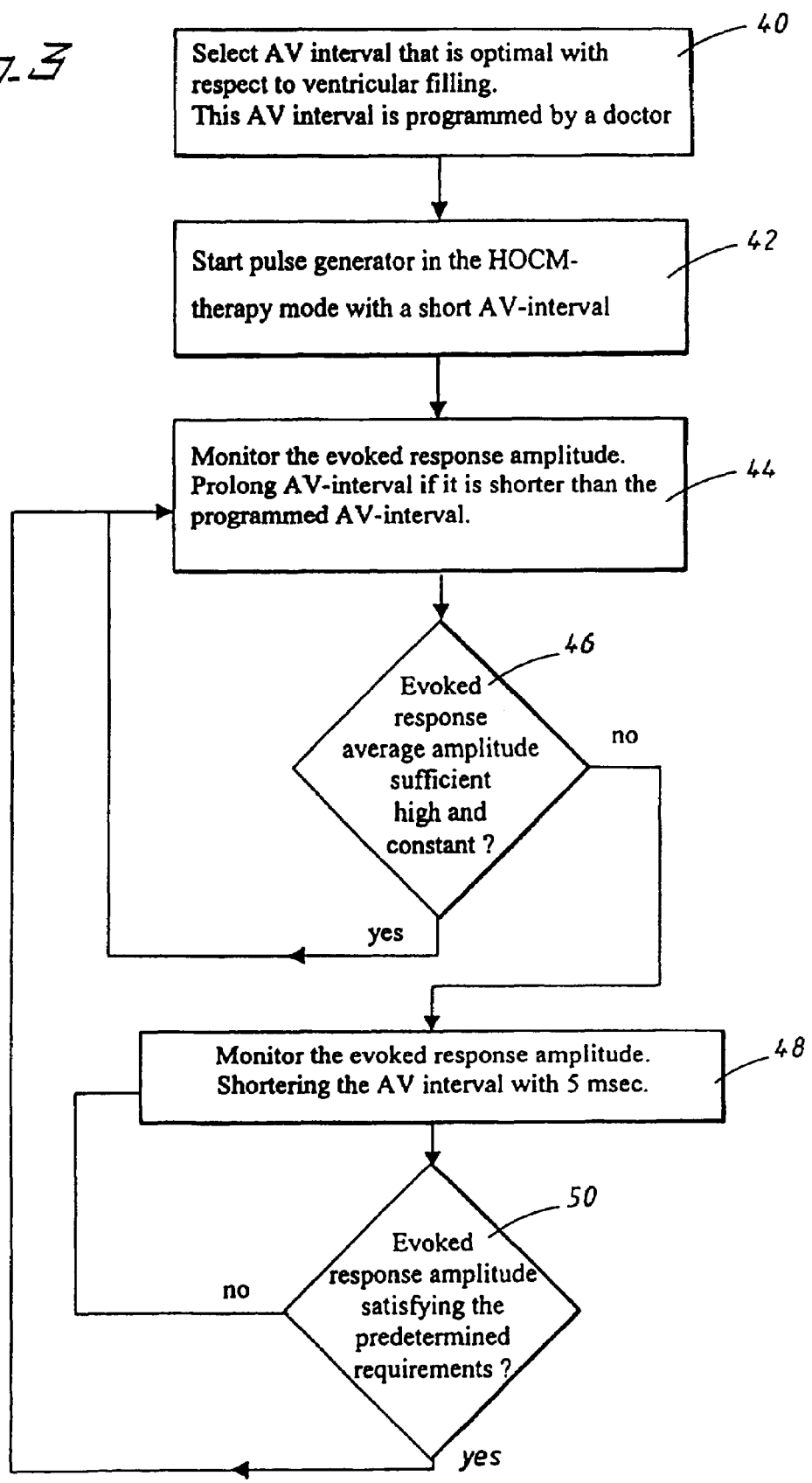

DUAL CHAMBER HEART STIMULATOR WITH EVOKED RESPONSE DETECTOR

BACKGROUND OF THE INVENTION

1. Field of the Invention

The present invention relates to a heart stimulator, particularly a dual chamber pacemaker with an evoked response detector.

2. Description of the Prior Art

For certain conditions such as hypertrophic obstructive cardiomyopathy (HOCM) the patient's condition may improve if he or she is paced 100% in the ventricle. In a state of HOCM the left ventricular wall is asymmetrically thickened. The interventricular septum thickness significantly exceeds that of the opposing posterolateral wall. A pressure gradient exists across the left ventricular outflow tract and during ventricular contraction, a progressive degree of outflow tract obstruction results. The conventional site of ventricular pacing is within the right ventricular apex and pacing, prior to intrinsic R-wave excitation, from this site can favorably alter the degree of obstruction. This has been clinically verified.

100% pacing in the ventricle requires understanding of a phenomenon referred to as fusion. Fusion means that the natural conduction time, which is the time interval between an atrial activity (a sensed P-wave or a delivered A-pulse) and the subsequent natural ventricular activity (R-wave), is the same as the time (AV-interval) between an atrial activity (again, a sensed P-wave or a delivered A-pulse) and the delivery of a ventricular stimulation pulse (V-pulse). Fusion is thus a condition where the V-pulse is delivered at the same time as the R-wave occurs. Thus, fusion means that the V-pulse occurs when the heart tissue is not capable of responding, i.e. it is refractory, a tissue refractory period starting at the depolarization event (R-wave) and remaining until repolarization (T-wave) occurs. Although not necessarily harmful to the heart, fusion causes loss of energy in the V-pulse, and should therefore be avoided to save pacemaker battery energy. In the discussion herein, both the time interval between a P-wave or an A-pulse, and a V-pulse will be referred to as the AV-interval.

To obtain 100% pacing beats with no fusion, very short AV delays have been used. Such very short AV intervals are, however, non-physiologic and therefore it is highly desirable to prolong the AV interval while maintaining a continuous monitoring of fusion, such that the AV interval would be shortened automatically if fusion beats appear. Several attempts have been made to solve this problem.

Thus, U.S. Pat. Nos. 5,534,016 and 5,713,930 describe techniques for optimizing the AV interval for therapeutic purposes for patients having HOCM. In the system according to U.S. Pat. No. 5,534,016 the T-wave detection is monitored to detect when the AV interval is lengthened to the point of evoking a fusion beat, and in the system disclosed in U.S. Pat. No. 5,713,930 the relationship between AV intervals and OT intervals (=the time interval between a delivered ventricular stimulus and resulting T-wave) is monitored and therefrom it is determined when AV intervals correspond to full capture and when AV intervals correspond to fusion.

Further, in U.S. Pat. No. 5,507,782 a dual chamber pacemaker is described in which the longest AV interval which results in complete ventricular capture is determined from the wave form of the ventricular depolarization R-wave following a ventricular pacing pulse for the purpose of treating patients suffering from HOCM. In this document the problems related to fusion beats and the transition region between complete pacing and fusion are not at all dealt with.

Another way of solving the problem of fusion and providing a 100% pacing of the ventricle is by AV node ablation. AV node ablation is, however, an intervention associated with extra costs and the conduction pathway from the atria to the ventricles is then permanently destroyed so the patient will be completely dependent on a pacemaker in the future with higher clinical risks in the event of a pacemaker failure.

SUMMARY OF THE INVENTION

An object of the present invention is to provide a heart stimulator suitable for treating HOCM patients by accomplishing 100% paced ventricular capture, which stimulator comprises a new type of evoked response detector suitable for detecting incipient fusion in a simple and reliable way.

The above object is achieved in accordance with the principles of the present invention in a heart stimulator having an atrial stimulator and a ventricular stimulator for producing stimulation pulses respectively for delivery to the atrium and the ventricle of a patient's heart, an atrial sensor for sensing atrial signals, an evoked response detector for detecting evoked response signals, a determination unit for determining an incipient fusion AV-interval from the sensed atrial signals and the detected evoked response signals and a control unit for controlling the ventricular stimulator to deliver ventricular stimulation pulses at a controlled AV-interval which is shorter than the incipient fusion AV-interval, wherein the evoked response detector includes an averaging unit which forms an average amplitude value of the evoked response signal during a predetermined time window of each cardiac cycle, and wherein a comparator compares this average value with predetermined limit criteria and supplies a comparison result to the determination unit to allow the determination unit to determine whether a detected evoked response signal results from an incipient fusion beat or a completely stimulated capture.

In the following the expression "sensed atrial signals" denotes sensed spontaneous atrial events P-waves as well as stimulated atrial events (A-pulses). The interval between a sensed spontaneous atrial event and the ventricular V-pulse is denoted by PV interval, and the interval between a stimulated atrial event and the ventricular V-pulse is denoted by AV interval. The PV interval is generally shorter than the AV interval. As noted above, however, as used herein the PV-interval as well as the AV-interval will be referred to as the AV-interval hereinafter.

Thus, in the stimulator according to the present invention the AV-interval is continuously monitored and automatically shortened if incipient fusion is detected. Incipient fusion is detected by an evoked response detector from measured ventricular signals picked up by an ventricular electrode and containing the evoked response signal, and the AV-interval will be adjusted accordingly to be as long as possible while avoiding the occurrence of fusion beats. From a hemodynamic point of view, e.g. ventricular filling and cardiac output, such a stimulator operation will give optimum results. Thus the stimulator according to the invention will operate with an AV-interval that is optimized with respect to hemodynamic conditions.

In an embodiment of the heart stimulator according to the invention, the control unit is adapted to modulate the AV-interval with a predetermined amount, and the comparator is adapted to compare the variation of the average amplitude values obtained during the time window with a predetermined limit. A large variability is then a clear indication of incipient fusion.

In another embodiment, the control unit is adapted to regularly prolong the AV-interval with a predetermined amount and the comparator is adapted to compare the average amplitude values obtained during the time window of cardiac cycles with the predetermined limit value and/or compare the variation of the average amplitude values obtained during the time window with a predetermined limit. In this way, incipient fusion can be detected at a very early stage and by utilizing both an amplitude criterion and a variability criterion improved reliability is obtained.

In a further embodiment of the heart stimulator according to the invention the evoked response detector is adapted to determine the DC level of the measured ventricular signal and subtract this DC level from each sample before the average value is formed. It is important to subtract the DC level from, the measured signal picked up by the electrode to get a corrected signal for subsequent analysis.

In another embodiment of the heart stimulator according to the invention a respiration signal determining unit is provided for determining a respiration signal representing the respiration rate of the patient, from a predetermined number of the average values.

DESCRIPTION OF THE DRAWINGS

FIG. 1 is a block diagram of the basic components of a heart stimulator constructed and operating in accordance with the principles of the present invention.

FIG. 2 is a block diagram of the evoked response detector of the heart stimulator according to the invention.

FIG. 3 is a flowchart illustrating the operation of the inventive embodiment shown in FIGS. 1 and 2.

DESCRIPTION OF THE PREFERRED EMBODIMENTS

Figure 4:
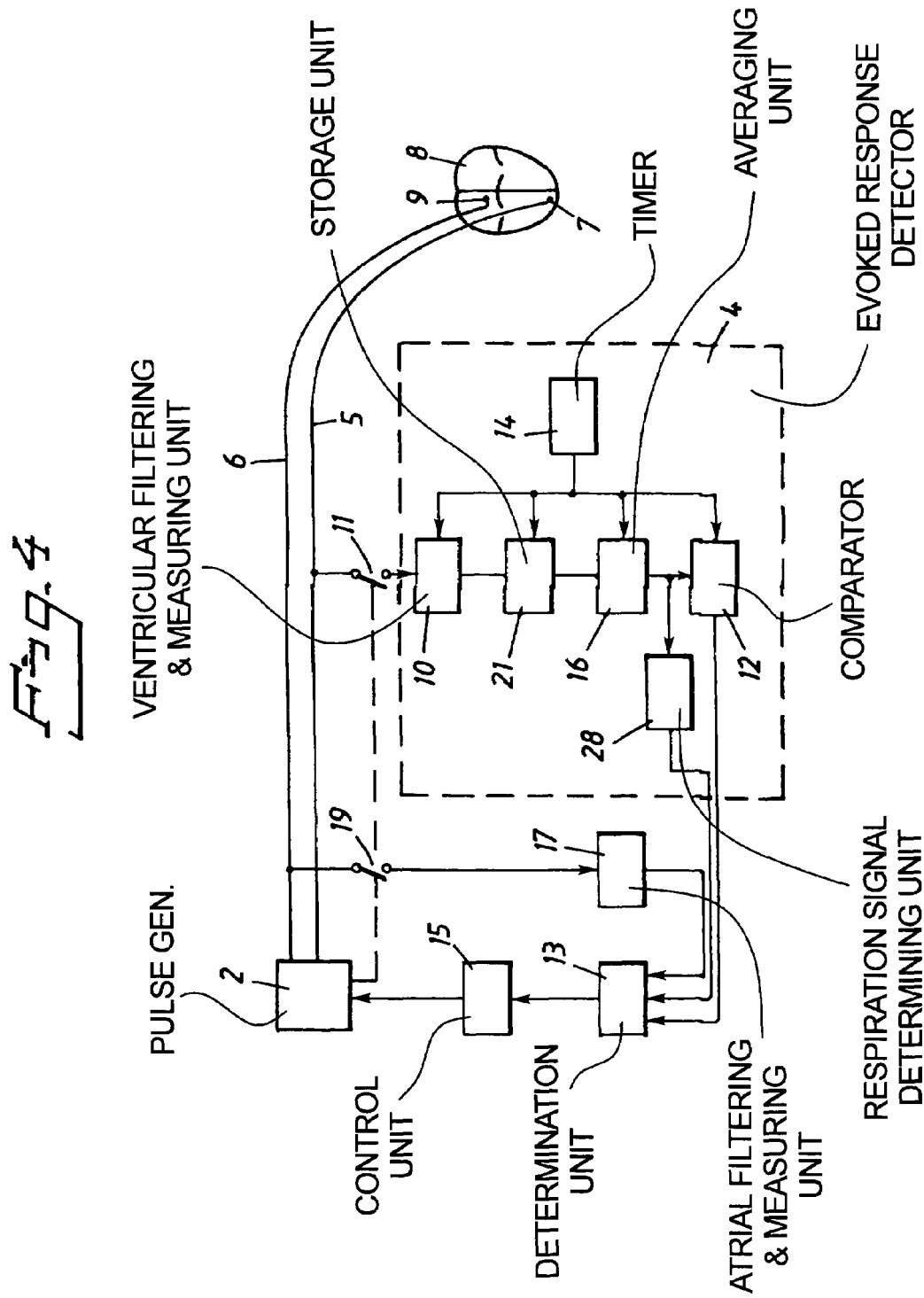
FIG. 4 is a block diagram of the basic components of a second embodiment of a heart stimulator constructed and operating in accordance with the principles of the present invention.

It is known to distinguish between completely stimulated captures, fusion beats and losses of capture from analysis of average amplitude values of recorded ventricular signals during a predetermined time window after a pacemaker stimulation, see Åsa Uhrenius et al., "Evaluation of new Algorithms for Autocapture with Unipolar Leads", CARDIOSTIM 98, Nice, June 1998.

FIG. 1 shows a block diagram of the basic components of the heart stimulator according to the invention. The stimulator has a pulse generator 2 which through leads 5, 6 and associated atrial and ventricular electrodes 7, 9 are connected to the heart 8 of a patient. The pulse generator 2 is devised to produce stimulation pulses of varying amplitudes which through the leads 5, 6 with their electrodes 7, 9 are transferred to the heart 8. An evoked response detector 4 of the above mentioned type is connected to the ventricular lead 5. An atrial detector having an atrial filtering and measuring unit 17 is connected to the lead 6 for measuring amplitudes of signals picked up by the atrial electrode 9. A determination unit 13 is connected to the evoked response detector 4 and to the atrial filtering and measuring unit 17 for determining an incipient fusion AV-interval, i.e. the AV-interval at which incipient fusion was detected, from the measured atrial signals and detected incipient fusion beats.

A control unit 15 is connected to the determination unit 13 and to the pulse generator 2 for controlling the pulse generator 2 to deliver stimulation pulses at a controlled AV interval which is shorter than the incipient fusion AV-interval.

The atrial filter and measurement unit 17 and the evoked response detector 4 are disconnected by switches 19 and 11 from their respective leads 5, 6 during stimulation.

The evoked response detector 4 has filter and measuring unit 10. The filtered ventricular signals picked up by the ventricular electrode 7 are supplied to a storage unit 21, an averaging unit 16 and to a comparator 12 for detecting incipient fusion by comparing the average amplitude obtained during a predetermined time window of the cardiac cycle from the averaging unit 16 with suitably selected limit values. As follows from the above mentioned publication by Åsa Uhrenius et al. completely stimulated captures result in a comparatively large constant average amplitude whereas an incipient fusion results in a decrease of the absolute value of this average amplitude.

As an alternative, the averaging unit 16 can be adapted to form a running average value of the measured ventricular signals during the predetermined time window from a predetermined number of the latest cardiac cycles and the comparator 12 can be adapted to receive the running average value and compare the average value obtained during the time window of each cardiac cycle with the running average value from immediately preceding cardiac cycles.

The above mentioned limit values of the comparator 12 can be selected such that e.g. a 10% decrease of the measured average amplitude compared to the average amplitude in a situation of completely stimulated capture is indicated as an incipient fusion. Thus, a decrease of the absolute value of the average amplitude from e.g. 26 mV to e.g. 23, 5 mV can be interpreted as incipient fusion. In this case, a running-average value as described above of e.g. the ten last cardiac cycles, is suitably used as limit value in the comparator 12 for obtaining an acceptable signal-to-noise ratio.

A timer 14 is provided for determining the evoked response time window during which the ventricular signal is measured and stored. This evoked response window normally extends from 15 to 55 msec after stimulation.

Thus, after a blanking time of about 15 msec the measured evoked ventricular signal is sampled and digitized during this evoked response time window and the average value of these samples is formed. This procedure is performed in the averaging unit 16, which thus supplies to the comparator 12 an average amplitude value obtained during the time window for each heart beat. A suitable sampling frequency can be e.g. 512 Hz, which results in about 20 samples per beat.

As also follows from the publication by Åsa Uhrenius et al., the variation in the average amplitude from different cardiac cycles is comparatively small in a situation of completely stimulated capture, whereas this variation increases in a fusion situation. Thus, as an alternative embodiment, the comparator 12 can be adapted to compare the variability of average amplitude values obtained from different cardiac cycles with a predetermined variability limit to detect an incipient fusion.

The variability criterion for indicating incipient fusion normally should be more strict than the above discussed amplitude criterion. Thus, a variability increase in the average amplitude values of e.g. 25% compared to the variability at completely stimulated capture can be used as variability criterion in the comparator 12 for indicating incipient fusion. An increase of the peak to peak variability in the average amplitude values from different cardiac cycles from e.g. 2.5 mV to e.g. 3.0 mV can be interpreted as incipient fusion. Also is this case a running average value from e.g. the ten latest cardiac cycles should preferably be used.

As a further version of this embodiment, the control unit 15 can be adapted to carefully modulate the AV-interval with e.g. ±5 msec or ±10 msec. A large variability appearing in the average amplitudes is then a reliable indication of fusion.

As still another alternative, the control unit 15 can be adapted to prolong at regular intervals the AV-interval with a predetermined amount, e.g. 10 msec, and the average amplitude or variability criteria described above are checked. If the average amplitude or variability criteria then, for this prolonged AV-interval, indicate fusion or incipient fusion, the AV-interval is shortened by 20 msec. If no changes in average amplitude or variability are noted, the AV-interval is the correct one. This would mean that the heart stimulator chooses an AV-interval which is approximately 20 msec shorter than the AV-interval at which incipient fusion is detected. In this way, a type of check is performed to determine if the heart stimulator operates close to fusion, and in this way incipient fusion can be detected at a very early stage.

In the heart stimulator according to the invention it is also possible to utilize both above described amplitude and variability criteria for determining an incipient fusion which normally further improves the detection reliability.

To obtain a reliable result it is also desirable to eliminate any DC level in the measured ventricular signal. This can be performed by sampling the measured ventricular signal before the emission of a stimulation pulse and forming an average value of these samples during a cardiac cycle. This average value represents the DC level and is subtracted from each sample of the subsequent measured ventricular signal.

FIG. 2 shows in greater detail one embodiment of the evoked response detector of the heart stimulator according to the invention. The ventricular signal picked up by the lead 5 with its electrode 7 in FIG. 1 is supplied to a highpass filter 20. An amplifier 22 and an A/D converter 24 are provided for amplifying and A/D converting respectively the filtered signal. A digital signal processor 26 calculates the average amplitudes of the measured ventricular signals and compares them with suitably selected limit values as described above for detecting an incipient fusion.

FIG. 3 is a flow chart illustrating the function of the embodiment illustrated in FIGS. 1 and 2 of the heart stimulator according to the invention for achieving 100% paced ventricular capture while optimizing the AV-interval with respect to hemodynamic conditions. In step 40 an AV interval is selected which is optimal with respect to the ventricular filling of the patient in question. This AV interval is programmed by a doctor. The pulse generator 2 starts the HOCM therapy mode with a short AV-interval, step 42.

The evoked response signal average amplitude during each heart beat is monitored by the evoked response detector 4, and the AV interval is prolonged if it is shorter than the programmed AV interval, step 44.

It is checked that the evoked response average amplitude has a sufficiently high, substantially constant absolute value, in step 46. If so, the AV-interval is prolonged while monitoring the evoked response amplitude according to step 44. If not, the AV-interval is shortened with e.g. 5 msec while monitoring the evoked response amplitude, at step 48.

It is then checked whether the average value formed from sampled values of the evoked response signal as described above maintains a sufficiently high and constant absolute value according to the predetermined requirements, in step 50. If so, the procedure reverts to step 44, viz. the AV-interval is once again prolonged, provided that it is shorter than the programmed AV-interval, while monitoring the evoked response amplitude, and the procedure is continued to step 46 as described above. If not, the procedure reverts to step 48, viz, the AV-interval is further shortened with 5 msec while monitoring the evoked response amplitude.

Thus the heart stimulator according to the invention is operating at an AV-interval which is as close as possible to the optimal AV-interval programmed by a doctor while securing all the time that occurrence of fusion is avoided. In this way a continuous suboptimization is obtained of the programmed optimal AV-interval set by the doctor. If the evoked response average amplitude does not satisfy predetermined criteria with respect to the absolute averaged value of the amplitude and possibly the variability of the amplitude, the AV-interval is automatically shortened until these criteria are again satisfied.

FIG. 4 is a block diagram of the basic components of a second embodiment of the heart stimulator according to the invention.

This embodiment has, in addition to the elements of the embodiment shown in FIG. 1, a respiration signal determining unit 28, which is supplied with the average signal values generated by the averaging unit 16. The respiration signal determining unit 28 generates a respiration signal, representing the respiration rate of the patient, from a predetermined number of evoked response average values. The respiration signal is supplied to the AV-interval determining unit for use in the control of the pulse generator 2. The use of the respiration rate to control the operation of a pacemaker, is well known to the person skilled in the art, cf. e.g. U.S. Pat. No. 4,702,253, and is therefore not described herein.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator comprising:
   a stimulation pulse generator adapted for interaction with an atrium and a ventricle of a heart for generating atrial stimulation pulses and ventricular stimulation pulses having an associated AV-interval;
   an atrial sensor, adapted for interaction with said atrium, for sensing atrial signals therefrom;
   an evoked response detector adapted for interaction with said ventricle for receiving ventricular signals, for detecting evoked response signals and including an averaging unit which forms an average amplitude value of respective evoked response signals during a predetermined time window of each cardiac cycle, said average amplitude values exhibiting a variability from cardiac cycle to cardiac cycle, and a comparator which compares said average amplitude value for each cardiac cycle with a predetermined variability limit, to generate a comparison result;
   a determination unit connected to said evoked response detector and to said atrial sensor, which determines an incipient fusion AV-interval to be present if said comparison result indicates said variability limit was exceeded; and
   a control unit connected to said determination unit and to said pulse generator for controlling timing of said ventricular pulses to produce a controlled AV-interval which is shorter than said incipient fusion AV-interval to maintain 100% stimulated beating of said heart.

2. A heart stimulator as claimed in claim 1 wherein said control unit modulates said AV-interval by a predetermined amount, to obtain a modulated AV-interval, and wherein said comparator compares respective average amplitude values for respective cardiac cycles wherein the modulated AV-interval was in effect, to said predetermined variability limit value.

3. A heart stimulator as claimed in claim 2 wherein said control unit regularly prolongs said AV-interval by said predetermined amount, to obtain said modulated AV-interval.

4. A heart stimulator as claimed in claim 1 wherein said evoked response detector samples and digitizes said evoked response signals for each heartbeat in a predetermined evoked response time window beginning at a predetermined time after delivery of a stimulation pulse from said pulse generator to said ventricle, thereby obtaining sampled amplitude values, and wherein said averaging unit forms said average amplitude value from said sampled amplitude values.

5. A heart stimulator as claimed in claim 4 wherein said evoked response detector samples and digitizes said evoked response signals with a sampling frequency and with a length of said evoked response time window so that approximately 20 of said sampled amplitude values are obtained within each evoked response time window.

6. A heart stimulator as claimed in claim 5 wherein said evoked response detector determines a DC level of said ventricular signals and subtracts said DC level from sampled amplitude value, before said averaging unit forms said average amplitude value.

7. A heart stimulator as claimed in claim 1 further comprising a respiration signal determining unit which determines a respiration signal associated with said patient, representing a respiration rate, from a predetermined number of said average amplitude values, and supplies said respiration signal to said determination unit, and wherein said determination unit generates said determination result dependent on said respiration signal.

8. A heart stimulator as claimed in claim 7 wherein said respiration signal determination unit determines said respiration signal from variations among a predetermined number of said average amplitude values.

* * * * *